United States Patent

Bonometti et al.

[11] 4,189,570
[45] Feb. 19, 1980

[54] DIFLUORO-S-TRIAZINYLAMINO-HYDROXYNAPHTHALENE-SULFONIC ACID

[75] Inventors: Emil Bonometti, Basel; Herbert Seiler, Riehen, both of Switzerland

[73] Assignee: Ciba-Geigy Corporation, Ardsley, N.Y.

[21] Appl. No.: 841,762

[22] Filed: Oct. 13, 1977

[30] Foreign Application Priority Data

Oct. 21, 1976 [CH] Switzerland ............ 13307/76

[51] Int. Cl.² ......................................... C07D 251/44
[52] U.S. Cl. .................................. 544/211; 260/153
[58] Field of Search ........................................ 544/211

[56] References Cited

U.S. PATENT DOCUMENTS 3,945,989  3/1976  Angliker et al. .............. 544/211

FOREIGN PATENT DOCUMENTS 1644208  9/1970  Fed. Rep. of Germany .
1188606  4/1970  United Kingdom .

Primary Examiner—Alan L. Rotman
Assistant Examiner—Robert T. Bond
Attorney, Agent, or Firm—Prabodh I. Almaula

[57] ABSTRACT

Process for producing compounds of the formula

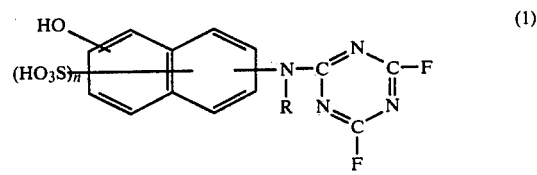

(1)

wherein R is hydrogen, methyl or ethyl, and n is 1 or 2, which process comprises condensing aminohydroxynaphthalenesulphonic acids of the formula

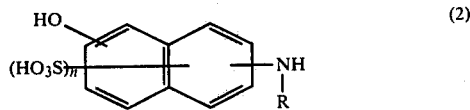

(2)

with 2,4,6-trifluoro-s-triazine, in an aqueous solution or suspension, within a pH range which is defined by $$pK_{N(R)H} \leq pH \leq (pK_{OH} - 2)$$

wherein $pK_{N(R)H}$ and $pK_{OH}$ are the pK values respectively of the amino group and hydroxyl group of the aminohydroxynaphthalenesulphonic acid and pH is the hydrogen exponent, to give compounds of the formula (1).

4 Claims, No Drawings

DIFLUORO-S-TRIAZINYLAMINO-HYDROXYNAPHTHALENE-SULFONIC ACID

The direct monoacylation of 1-amino-8-hydroxynaphthalene-3,6-disulphonic acid (H-acid) with cyanuric chloride on the amino group of the H-acid has to be performed in a strongly acid solution in order to avoid secondary reactions. With cyanuric fluoride instead of cyanuric chloride, the direct monoacylation of H-acid in strongly acid solution is however not possible since the more reactive cyanuric fluoride under such reaction conditions becomes excessively hydrolysed and is hence lost for the desired reaction. In the neutral region, on the other hand, the monoacylation of H-acid with cyanuric fluoride leads to a large amount of by-product which is formed by condensation of the cyanuric fluoride with the hydroxyl group of the H-acid.

It has now been found that H-acid, and also other aminohydroxynaphthalenesulphonic acids, can be monoacylated with cyanuric fluoride, homogeneously and in high yield, if the reaction is performed in a pH range in which—by virtue of the predetermined pK values of the aminohydroxynaphthalenesulphonic acid—less than 50% of the amino group of the aminohydroxynaphthalenesulphonic acid is in the protonised form and less than 1% of the hydroxyl group of the aminohydroxynaphthalenesulphonic acid in the deprotonised form, i.e. above the pK value of the amino group and at least 2 pH units lower than the pK value of the hydroxyl group. The pK values in this case are the known negative common logarithms of the acid constant and base constant in the protolysis equilibrium of the hydroxyl group and amino group, respectively, of the aminohydroxynaphthalenesulphonic acid in aqueous solution; the pH value is the hydrogen exponent.

The following may be mentioned as aminohydroxynaphthalenesulphonic acids which can be monoacylated homogeneously and with high yield in the aforementioned manner with cyanuric fluoride:
1-amino-5-hydroxynaphthalene-7-sulphonic acid,
1-amino-8-hydroxynaphthalene-4-sulphonic acid,
2-amino-5-hydroxynaphthalene-7-sulphonic acid,
2-amino-6-hydroxynaphthalene-8-sulphonic acid,
2-amino-8-hydroxynaphthalene-6-sulphonic acid,
2-methylamino-5-hydroxynaphthalene-7-sulphonic acid,
2-ethylamino-5-hydroxynaphthalene-7-sulphonic acid,
2-methylamino-8-hydroxynaphthalene-6-sulphonic acid,
2-ethylamino-8-hydroxynaphthalene-6-sulphonic acid,
1-amino-6-hydroxynaphthalene-3,8-disulphonic acid,
1-amino-8-hydroxynaphthalene-3,6-disulphonic acid,
1-amino-8-hydroxynaphthalene-4,6-disulphonic acid,
2-amino-5-hydroxynaphthalene-7,1-disulphonic acid, and
2-amino-8-hydroxynaphthalene-3,6-disulphonic acid.

From the above enumeration of possible starting materials hence follows, as subject matter of the present invention, a process for producing compounds of the formula

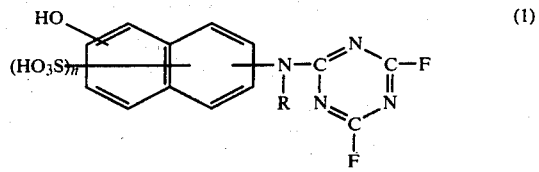

wherein R is hydrogen, methyl or ethyl, and n is 1 or 2, which process comprises condensing aminohydroxynaphthalenesulphonic acids of the formula

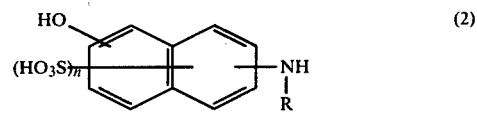

with 2,4,6-trifluoro-s-triazine, in an aqueous solution or suspension, within a pH range which is defined by $$pK_{N(R)H} \leqq pH \leqq (pK_{OH}-2),$$

wherein $pK_{N(R)H}$ and $pK_{OH}$ are the pK values respectively of the amino group and hydroxyl group of the aminohydroxynaphthalenesulphonic acid and pH is the hydrogen exponent, to give compounds of the formula (1).

A preferred embodiment of the process according to the invention comprises condensing 1-amino-8-hydroxynaphthalene-3,6-disulphonic acid with 2,4,6-trifluoro-s-triazine in an aqueous solution in the pH range of 3.5 to 5.

The compounds of the formula (1) obtained by the process according to the invention are valuable intermediate compounds for producing reactive dyes. Of particular value is the N-monoacylation product obtained from H-acid and cyanuric fluoride, which product can, in any desired sequence, be coupled with a coupling component and condensed with an amino compound, thus yielding brilliant red monofluoro-s-triazine dyes which are especially suitable for application by the continuous dyeing process.

Except where otherwise stated in the following Examples, parts are given as parts by weight, and the temperature values are in degrees Centigrade.

EXAMPLE 1

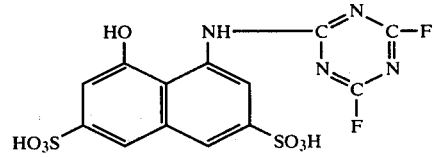

319 parts of 1-amino-8-hydroxynaphthalene-3,6-disulphonic acid are suspended in 2000 parts by volume of water at 15°, and with the addition of 100 parts by volume of 10 N sodium hydroxide solution dissolved at pH 6. To this solution are added 1500 parts of ice; and there are subsequently added dropwise at 0°, with thorough stirring, 135 parts of 2,4,6-trifluoro-1,3,5-triazine. The pH value falls rapidly to 4.5 and is held at this value by the continuous addition of 2 N sodium hydroxide solution. After completion of the addition, stirring is maintained for a further 5 minutes, and the content is determined by titration.

Result: content of uncondensed 8-amino-1-hydroxynaphthalene-3,6-disulphonic acid under 1%; yield of 1-(4',6'-difluoro-1',3',5'-triazin-2'-yl)-amino-8-hydroxynaphthalene-3,6-disulphonic acid = 97%.

It is possible in the same manner to react also 1-amino-8-hydroxynaphthalene-4,6-disulphonic acid with 2,4,6-trifluoro-1,3,5-triazine.

EXAMPLE 2

A suspension of the diazo compound produced, in the customary manner, from 17.3 parts of 2-aminobenzenesulphonic acid is added to 450 parts by volume of a solution, obtained according to Example 1, containing 47.8 parts of the disodium salt of 1-(4',6'-difluoro-1',3',5'-triazin-2'-yl)-amino-8-hydroxynaphthalene-3,6-disulphonic acid. The pH value during coupling is kept at 5.5. After completion of coupling, 9.3 parts of aminobenzene are added, and stirring is maintained at 15° to 20° with a pH value of 7 to 7.5 until no further aminobenzene is detectable. By the sprinkling in of sodium chloride, the red dye is precipitated and is then filtered off and dried.

EXAMPLE 3

9.3 parts of aminobenzene are added to 450 parts by volume of a solution, produced according to Example 1, containing 47.8 parts of the disodium salt of 1-(4',6'-difluoro-1',3',5'-triazin-2'-yl)-amino-8-hydroxynaphthalene-3,6-disulphonic acid. Whilst thorough stirring is maintained, the acid being liberated during condensation is neutralised with 2 N sodium hydroxide solution so that the pH value of the solution is held at 5.5 to 6. After completed condensation, a diazo compound prepared, in the usual manner, from 17.3 parts of 2-aminobenzenesulphonic acid is added, and coupling is effected at pH 6 to 7. When no further diazo compound can be detected, the red dye which has formed is precipitated by sprinkling in sodium chloride, and is subsequently filtered off and dried. It is identical to the dye obtained according to Example 2.

EXAMPLE 4

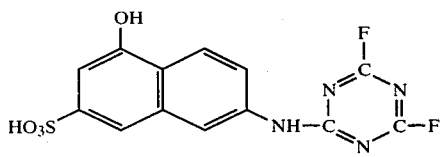

23.9 parts of 2-amino-5-hydroxynaphthalene-7-sulphonic acid are dissolved in 700 parts of water, with sodium hydroxide solution being added, at a pH value of 6. To this solution are added dropwise at a temperature of 0°–2°, within 15 minutes, 14.1 parts of 2,4,6-trifluoro-1,3,5-triazine, and the pH value is allowed to fall to 3.5. The pH value is kept between 3.5 and 4.5 by the subsequent dropwise addition of sodium hydroxide solution. After completed condensation, the reaction product which has precipitated can be filtered off or further processed with the suspension.

EXAMPLE 5

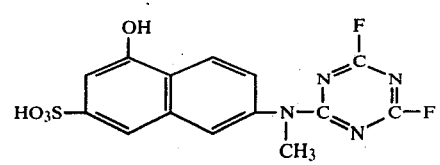

14.8 parts of 2,4,6-trifluoro-1,3,5-triazine are added dropwise, with good stirring, to the solution of 25.3 parts of 2-methylamino-5-hydroxynaphthalene-7-sulphonic acid in 700 parts of water at 0°–2°, and a pH value of 3.5–4.5 is maintained by continuous neutralising of the hydrogen fluoride being liberated. The course of reaction is followed chromatographically. The resulting solution of the intermediate is further processed immediately.

We claim:

1. The compound of the formula

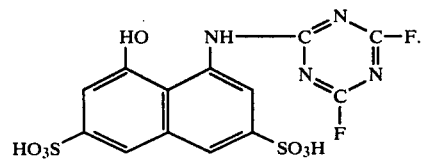

2. The compound of the formula

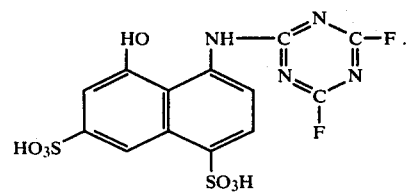

3. The compound of the formula

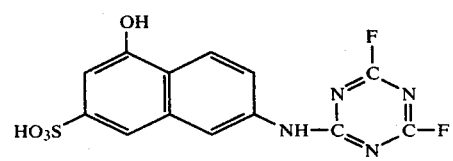

4. The compound of the formula

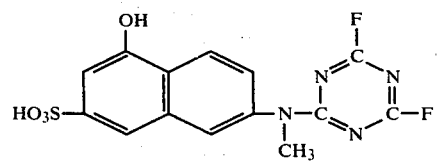

* * * * *